United States Patent [19]

Donno et al.

[11] Patent Number: 5,470,836

[45] Date of Patent: Nov. 28, 1995

[54] PAROMOMYCIN OR ITS DERIVATIVES OR SALTS THEREOF IN COMBINATION WITH SODIUM STIROGLUCONATE FOR PARENTERAL TREATMENT OF HUMAN PARASITIC DISEASES

[75] Inventors: Luigi Donno, Milan; Giuseppe Cassinelli, Voghera, both of Italy

[73] Assignee: Farmitalia Carlo Erba S.r.l., Milan, Italy

[21] Appl. No.: 354,017

[22] Filed: Dec. 5, 1994

Related U.S. Application Data

[63] Continuation of Ser. No. 86,565, Jul. 6, 1993, abandoned, which is a continuation of Ser. No. 943,139, Sep. 10, 1990, abandoned, which is a continuation of Ser. No. 598,611, Oct. 25, 1990, abandoned.

[30] Foreign Application Priority Data

Apr. 29, 1988 [GB] United Kingdom ............... 8810246

[51] Int. Cl.$^6$ ................................................. A61K 31/70
[52] U.S. Cl. ............................ 514/38; 514/23; 514/503; 536/13.3
[58] Field of Search ...................... 514/38, 53, 23, 514/503; 536/3.3

[56] References Cited

U.S. PATENT DOCUMENTS

| | | | |
|---|---|---|---|
| 2,916,485 | 12/1959 | Frohardt et al. | 536/13.3 |
| 3,065,147 | 11/1962 | Arcamone et al. | 536/13.3 |
| 4,021,601 | 5/1977 | Arcamone et al. | 536/13.3 |
| 4,125,707 | 11/1978 | Arcamone et al. | 536/13.3 |
| 4,337,248 | 6/1982 | Battistini et al. | 536/13.3 |

FOREIGN PATENT DOCUMENTS

| | | |
|---|---|---|
| 0090587 | 10/1983 | European Pat. Off. |
| 1464684 | 2/1977 | United Kingdom . |
| 2068367 | 8/1981 | United Kingdom . |

OTHER PUBLICATIONS

Journal of Antimicrobial Chemotherapy, vol. 14, No. 5, 1984, The British Society for Antimicrobial Chemotherapy, R. A. Neal et al.: "An in–vitro system for determining the activity of compounds against the intracellular amastigote form of Leishmania donovani", pp. 463–475.

Annals of Tropical Medicine and Parasitology, vol. 69, No. 3, 1975, N. M. Mattock et al.: "The experimental chemotherapy of leishmaniasis, II: The activity in tissue culture of some antiparasitic and antimicrobial compounds in clinical use", pp. 359–371.

Antimicrobial Agents and Chemotherapy, vol. 26, No. 5, Nov. 1984, American Society for Microbiology, J. El–On et al.: "Development of topical treatment for cutaneous Leishmaniasis caused by Leishmania major in experimental animals", pp. 745–751.

Pediatric Clinics of North America, vol. 32, No. 4, Aug. 1985, J. S. Seidel: "Treatment of parasitic infections", pp. 1077–1095.

Dermatologia Venezolana 24, 1986, pp. 82–84, Nuevo Tratamiento Para La Leishmaniasis Tegumentaria, Scorza, J. V. et al.

Ann. Trop. ed. Parasit., 1968, vol. 62, pp. 54–62, The effects of antibiotics of the neomycin group on experimental cutaneous leishmaniasis, R. A. Neal.

Rev. Cub. Med. Trop., 34, Jan.–Apr. 1982, pp. 34–45, Quimioterapia experimental en hamsteres, por paramomicina, contra dos aislados de Leishmania mexicana y Leishmania braziliensis, S. Rezzano et al.

Report on XIIth International Congress for Tropical Medicine and Malaria, Sep. 18–23, 1988, Amsterdam, Wes–4–4, Improved treatment of visceral leishmaniasis using a combination of aminosidine plus sodium stibogluconate, C. N. Chunge.

Primary Examiner—Douglas W. Robinson
Assistant Examiner—Elli Peselev
Attorney, Agent, or Firm—Oblon, Spivak, McClelland, Maier & Neustadt

[57] ABSTRACT

A compound of formula (I):

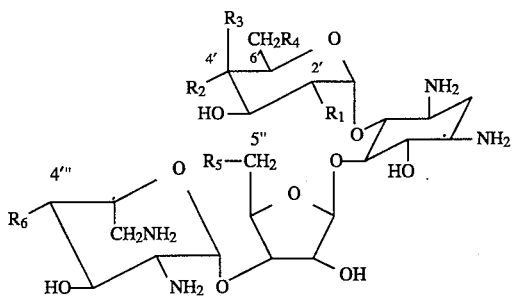

wherein:

$R_1$ is a hydroxy group or an amino group optionally substituted with a $C_1$–$C_4$ alkyl or phenyl-($C_1$–$C_4$) alkyl group, $R_2$ is hydrogen or a hydroxy group, $R_3$ is hydrogen or chlorine, $R_4$ is hydrogen or a hydroxy or amino group, $R_5$ is hydrogen or a hydroxy group, and $R_6$ is hydrogen or a hydroxy group, or a non-toxic acid addition salt thereof, is useful in the parenteral treatment of visceral leishmaniasis or malaria, and a synergistic composition comprising a compound of formula (I) or a non-toxic acid addition salt thereof and sodium stibogluconate is useful in the treatment of visceral leishmaniasis.

6 Claims, No Drawings

PAROMOMYCIN OR ITS DERIVATIVES OR SALTS THEREOF IN COMBINATION WITH SODIUM STIBOGLUCONATE FOR PARENTERAL TREATMENT OF HUMAN PARASITIC DISEASES

This application is a continuation of application Ser. No. 08/086,656, filed on Jul. 6, 1993, now abandoned, which is a continuation of 07/943,139, filed on Sep. 10, 1992, now abandoned, which is a continuation of 07/598,611, filed on Oct. 25, 1990, now abandoned, which was filed as International Application No. PCT/EP89/00461, filed on Apr. 26, 1989.

The present invention relates to paromomycin or a derivative or non-toxic acid addition salt thereof for use in the parenteral treatment of visceral leishmaniasis.

Leishmaniasis is included by W.H.O. among the six major tropical diseases against which a special programme was launched in 1974.

Human leishmaniasis is caused by at least 14 different species and subspecies of genus *Leishmania*, a flagellate protozoan parasite. The clinical manifestations of the disease depend on the infecting *Leishmania* organism and fall into three major forms: visceral, mucocutaneous and cutaneous. (Seventh Programme Report of Tropical Diseases Research, Chapter 7, The Leishmaniases - UNDP/World Bank, W.H.O. 1985).

Visceral Lieshmaniasis, in which the parasite invades internal organs such as the spleen, liver or bone marrow, is often fatal. The visceral disease, caused by *L. donovani, L. donovani infantum* and *L. chagasi*, is endemic in several parts of Africa, the Indian subcontinent and Latin America, and it occurs sporadically in China, the Mediterranean basin, South-West Asia and the Southern regions of the Soviet Union.

Few drugs are available for the treatment of Leishmaniases and those which are have been known for some time, namely pentavalent antimonials, considered and first-line drugs, and pentamidine or Amphotericin B, considered as second-line druges (McGreevy P. B. and Marsden P. D.: American Trypanosomiasis and Leishmaniasis, in chemotherapy of Parasitic Diseases, Campbell W. C. and Rew R. S. Eds, Plenum Press, New York and London, 1986). However, these drugs are fairly toxic and their activity is variable.

Sodium stibogluconate, used on its own in the treatment of visceral leishmaniasis, may give a cure rate of about 80% when administered parenterally in doses of 20 mg/kg body weight over 30 days. However, difficult cases due to primary unresponsivemess and/or relapse require additional treatment with allopurinol and the sodium stibogluconate for at least a further 30 days. This treatment requires prolonged hospitalisation.

Paromomycin I (Aminosidine) sulphate is an aminoglycoside antibiotic which became commercially available in the sixties. It is mainly used in humans by the oral route to treat diarrhoeal diseases, in the management of hepatic coma or preoperatively for bowel preparation. It is also used in the treatment of the infection of various tapeworms.

Being also directly amebicidal, Paromomycin I sulphate is also used as above and with other drugs to treat, by the oral route, asymptomatic as well as acute and chronic intestinal amebiasis. Due to its broad spectrum antibacterial activity it can also be used by the parenteral route (Gabbromycin (Trade Mark of Farmitalia Carlo Erba)) to treat infections caused by susceptible bacteria.

EP-A-90,587 describes a topical composition containing paromomycin sulphate, dimethylsulphoxide and/or quaternary ammonium salts for the treatment of cutaneous leishmaniasis.

It has now surprisingly been found that parenteral administration of paromomycin or certain derivatives thereof with pentavalent antimonials effective in the parenteral treatment or prophylaxis of visceral leishmaniasis gives an effective treatment against visceral leishmaniasis, especially in humans.

The present invention therefor provides a composition for use in the parenteral treatment of prophylaxis of visceral leishmaniasis comprising a compound of formula (I):

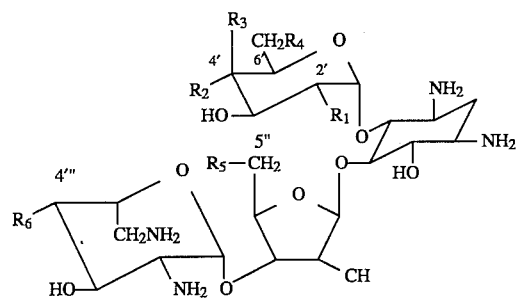

wherein:

$R_1$ is a hydroxy group or an amino group optionally substituted with a $C_1$–$C_4$ alkyl or phenyl ($C_1$–$C_4$) alkyl group, $R_2$ is hydrogen or a hydroxy group, $R_3$ is hydrogen or chlorine, $R_4$ is hydrogen or a hydroxy or amino group, $R_5$ is hydrogen or a hydroxy group, and $R_6$ is hydrogen or a hydroxy group, or a non-toxic acid addition salt thereof, a pentavalent antimonial effective in the parenteral treatment or prophylaxis of visceral leishmaniasis, and a pharmaceutically acceptable diluent.

The present invention further provides a composition suitable for parenteral administration for the treatment or prophylaxis of visceral leishmaniasis, which comprises a compound of formula (I) or a non-toxic acid addition salt thereof, sodium stibogluconate and a pharmaceutically acceptable diluent, the weight ratio of the compound of formula (I) or salt thereof to the sodium stibogluconate being from 1:9 to 9:1.

The present invention also provides use of a compound of formula (I) or a non-toxic acid addition salt thereof in the manufacture of a medicament for the parenteral treatment or prophylaxis of visceral leishmaniasis, wherein the medicament additionally comprises a pentavalent antimonial effective in the parenteral treatment or prophylaxis of visceral leishmaniasis.

The compounds of formula (I) and salts thereof are agents for treating visceral leishmaniasis. They may be used to alleviate the condition of a patient, typically a human patient, suffering from visceral leishmaniasis. In formula (I) examples of suitable groups represented by $R_1$ are ethylamino and phenylpropylamino groups. Preferred compounds are shown in the following Table, after which the references previously describing them are also given. These references are herein incorporated by reference.

| Name | $R_1$ | $R_2$ | $R_3$ | $R_4$ | $R_5$ | $R_6$ | Ref. |
|---|---|---|---|---|---|---|---|
| 1) PAROMOMYCIN I | —$NH_2$ | —OH | —H | —OH | —OH | —OH | 1.2 |
| 2) 2'-N-ETHYL PAROMOMYCIN | —NH—$CH_2CH_3$ | —OH | —H | —OH | —OH | —OH | 3 |
| 3) 2'-N-(3-PHENYL) PAROMOMYCIN I | —NH—$CH_2$—$CH_2CH_2$—PH | —OH | —H | —OH | —OH | —OH | 3 |
| 4) 6'-DEOXY PAROMOMYCIN I | —$NH_2$ | —OH | —H | —H | —OH | —OH | 4 |
| 5) 6',5"-DIDEOXY- PAROMOMYCIN I | —$NH_2$ | —OH | —H | —H | —H | —OH | 4 |
| 6) COMPOUND 224 4-O-(6-amino-6-deoxy-α-D-glucopyranosyl)-5-O-[3-O-(2,6-diamino-2,6-dideoxy-β-L-ido-pyranosyl)-β-D-ribofuranosyl]-2-deoxy streptamina | —OH | —OH | —H | —$NH_2$ | —OH | —OH | 5 |
| 7) 4'-DEOXYPAROMOMY- CIN I | —$NH_2$ | —H | —H | —OH | —OH | —OH | 6 |
| 8) 4'-DEOXY-4'- EPICHLORO- PAROMOMYCIN I | —$NH_2$ | —H | —Cl | —OH | —OH | —OH | 6 |
| 9) 4'-4"-DIDEOXY- PAROMOMYCIN I | —$NH_2$ | —H | —H | —OH | —OH | —H | 7 |

1. Frohardt et al. U.S. Pat. No. A-2,916,485
2. Arcamone et al. U.S. Pat. No. A-3,065,147
3. F. Arcamone and G. Cassinelli, U.S. Pat. No. A-4,021,601 (May 3, 1977)
4. F. Arcamone and G. Cassinelli, GB-A-1,464,684 (June 15, 1977)
5. F. Arcamone and G. Cassinelli, U.S. Pat. No. A-4,125,707 (Nov. 14, 1978)
6. C. Battistini, G. Cassinelli et al, U.S. Pat. No. A-4,337,248 (June 29, 1982)
7. C. Battistini, G. Cassinelli et al, GB-A-2,068,367 (Aug. 12, 1981).

The other derivatives may be prepared by obvious modifications of the synthetic methods described in these references.

The preferred compound of formula (I) is paromomycin, and the preferred salt is the sulphate. The most preferred compound is paromomycin sulphate. The parenteral administration may be, for example, intramuscular or intravenous administration.

Conventional diluents such as Water for Injections may be used. The composition may be formulated and administered in a manner conventionally employed in the art. The composition may also comprise other agents effective in the parenteral treatment or prophylaxis of visceral leishmaniasis.

It is surprisingly possible to treat successfully a greater proportion of subjects suffering from visceral leishmaniasis with a mixture of the compound of formula (I) and sodium stibogluconate than with either compound separately.

The compound of formula (I) or salt thereof and the sodium stibogluconate are generally administered in a weight ratio from 1:9 to 9:1, preferably 3:7 to 7:3, more preferably 4:6 to 6:4. An especially preferred weight ratio is about 4:5, such that the compound of formula (I) or salt thereof may be administered in an amount of about 16 mg/kg body weight/day and the sodium stibogluconate may be administered in an amount of about 20 mg/kg body weight/day.

The composition of the present invention may be prepared by simply mixing together all the components.

A suitable method of treatment of visceral leishmaniasis comprises administering parenterally to a subject suffering or liable to suffer therefrom an effective amount of a compound of formula (I) or a non-toxic acid addition salt thereof and a pentabalent antimonial effective in the parenteral treatment or prophylaxis of visceral leishmaniasis.

A further suitable method of treatment of visceral leishmaniasis comprises administering parenterally to a subject suffering or liable to suffer therefrom synergistically effective amounts of a compound of formula (I) or a non-toxic acid addition salt thereof and sodium stibogluconate.

A suitable dosage range for the parenteral route is from 1 to 50 mg/kg body weight/day, preferably 10 to 20 mg/kg body weight/day, more preferably about 14 to 16 mg/kg body weight/day, of the compound of formula (I) or salt thereof for the treatment of visceral leishmaniasis. The sodium stibogluconate may be administered parenterally in amounts conventially used, for example about 20 mg/kg body weight/day.

The present invention also provides a process for preparing pharmaceutical compositions containing a compound of formula (I) or a non-toxic acid addition salt thereof and a pentavalent antimonial effective in the parenteral treatment or prophylaxis of visceral leishmaniasis as active agents, characterized in that the active agents, which have been prepared in known ways, are admixed with a pharmaceutically acceptable diluent and then transformed to a pharmaceutical preparation suitable for treating visceral leishmaniasis.

The efficacy of compositions of the present invention for parenteral treatment of visceral leishmaniasis, has been demonstrated by the comparative clinical trials in the following Examples. The drug used was Gabbromycin supplied by Farmitalia Carlo Erba, comprising:

(a) Vial containing Paromomycin I sulphate 500 mg
(b) Ampoule containing Water for Injections 4 ml

EXAMPLE 1

Studies in Human Leishmaniasis

Studies in human patients have been carried out in respect of visceral leighmaniasis.

A comparative trial, carried out in patients affected by visceral leishmaniasis with sodium stibogluconate (Pentostam (Trade Mark)) alone (20 mg/kg b.w./die for more than 20 days), Gabbromycin alone (16 mg/kg b.w./die for 20 days maximum 1 g per day) or a combination of the two drugs for 14 days administered by the intramuscular route, has given the following results (shown in Table 1): Pentostam alone cured 10/13 patients, but 3/10 of patients cured had a relapse within 2 months after the end of the therapy. Gabbromycin alone cured 10/12 patients with out any relapses among the cured patients. The combination cured 16/16 patients with one relapse in a patient treated for only 11 days but the patient was definitely cured after a second cycle of treatment.

prothrombin time: and spleen aspirate smear examination by the method of Chulay & Bryceson, Quantitations of amastigotes of leishmania donovani in smears of splenic aspirates from patients with visceral leishmaniasis, American Journal of Tropical Medicine and Hygiene, 32, 1983, 475–479.

Follow-up examinations were given 2 and 6 months after termination of treatment, since relapses after this period were found to be rare (Manson Bahr, East Africa kala-azar with special reference to the pathology, prophylaxis and treatment, Transactions of the Royal Society of Tropical Medicine and Hygiene, 53, 1956, 123–137, and Oster, Advances in clinical diagnosis and chemotherapy of leishmaniasis in Kenya, Insect Science Applications, 7, 1968, 235–240).

Treatment of effectiveness was graded under the following headings:

Clinical cure: complete abatement of initial symptoms with marked reduction of spleen size;

TABLE 1

| | | Paromomycin I sulphate in visceral leishmaniasis | | | | |
|---|---|---|---|---|---|---|
| DRUG | NUMBER OF PATIENTS | DOSAGE SCHEDULE | DAYS OF TREATMENT | NUMBER OF PATIENTS CURED | % PATIENTS CURED | NUMBER OF RELEASES |
| PENTOSTAM | 13 | 20 mg/kg/day i.m. | 20 | 10 | 77 | 3 (30%) |
| GABBROMYCIN | 12 | 16 mg/kg/day i.m. Maximum: 1 g | 20 | 10 | 84 | 0 |
| PENTOSTAM + GABBROMYCIN | 16 | 20 mg/kg/day + 16 mg/kg/day i.m. | 14 | 16 | 100 | 1* |

*Patient treated only for 11 days and cured definitively after a second complete cycle of therapy

EXAMPLE 2

Studies in Human Leishmaniasis

Patients newly diagnosed with visceral leighmaniasis, confirmed by the presence of leishmaniasis amastigotes in spleen aspirates, were allocated randomly to groups subjected to the following treatments:

1) IV/IM sodium stibogluconate (SbV) 20 mg/kg body weight once per day;

2) IM paromomycin sulphate (PM) 14–16 mg/kg body weight once per day;

3) IV/IM sodium stibogluconate 20 mg/kg body weight once per day and paromomycin sulphate 14–16 mg/kg body weight once per day.

All treatments were administered until the first negative spleen aspirate was obtained, or for 20 consecutive days regardless of aspirate findings.

Exclusion criteria were: age 3 years; known allergy to aminoglycoside compounds: pregnancy; haemoglobin assay below 40 g/l; abnormal prothrombin time; impaired liver or renal function; major concurrent infection; previous drug treatment for leishmaniasis; and spleen smear-parasite grading of less than 4+.

The following procedures were conducted for patient assessment at intake and at suitable intervals during and after treatment: clinical history writeup: physical examination: body weight: chest X-ray: ECG tracing: liver and kidney function tests: blood picture and blood smears (to rule out malaria): complete urinalysis: stool examination:

Partial cure: persistence of low parasite counts in terminal spleen aspirates;

Apparent cure: negative spleen aspirate smears at termination of treatment;

Relapse: reappearance of leishmanial parasites after an apparent cure;

Definite cure: persisting clinical cure with negative spleen aspirates 6 months after termination of treatment;

Failures: partial cures and relapses.

Drug safety was assessed for each treatment regime in terms of incidence of drug-related signs and symptoms and of laboratory test results return abnormalities. The assembled data were processed statistically by the Fisher's exact test (chi-square) and Pearson's correlation coefficient.

Results

A total of 56 patients were entered. Of these, two died during the follow-up period, one from fulminating oral thrush and one from trauma, and one patient failed to report. This left 53 assessable patients, namely 37 males and 16 females, age range 3–36 years, mean age 18. Clinical manifestations at intake were fever, weakness, enlarged liver and spleen, pallor, and tachycardia in all patients; plus malnutrition in 95%, cough in 62%, jaundice in 25% and ankle oedema in 14%. Complicating factors present at intake or emerging in the course of treatment included epistaxis, pneumonia, uveltis throat infection, and chest pain, as reported in Chung et al., Complications of kala-azar and its treatment in Kenya, East African Medical Journal, 61, 1984, 120–127.

Fever was the first symptom to abate, usually after 24 to 60 hours of starting treatment; splenomegaly was the last. At 2 and 6 month follow-up examination, the spleen was still moderately enlarged respectively in 20 and 5% of treated patients. Body weight tended to drop in the first 10 days of treatment and pick up later, to return to normal by the first (2 month) re-check (Table 2). Ankle oedema abated in the first 10 days of treatment.

The incidence of epistaxis was significantly reduced by treatment with vitamin K (10 mg daily for 5 days) in patients with low initial haemoglobin assays and prolonged prothrombin time readings. Uveitis with ocular pain and blurred vision was present at intake in 22.5% of the patients; it abated without specific treatment as visceral leishmaniasis was cured. Bouts of pneumonia developed in 9 cases (17%). Of these, 5 were on SbV alone and required antibiotic treatment; the remaining 4 were receiving PM and did not need additional antibiotic medication.

Initial hematologic disorders (Table 2) consisted for the most part of depressed hematopolesis (WHO Expert Commitee on Leishmaniasis, Technical Report Series 70, 1984) and pancytopenia (Kasli, Haematological abnormalities in visceral leishmaniasis, East African Medical Journal, 57, 1980, 634–640; Wasunna et al., Haematological changes in patients with visceral leishmaniasis, Proceedings of the 12th International Congress of Tropical Medicine and Malaria, Abstract ThP 5-3, page 270); both features showed improvement as the underlying leishmaniasis was cured. All patients had zero eosinophil counts at intake; the reappearance of peripheral blood was taken to connote a good prognosis (Lyerly et al., Eosinophilis as prognostic indicator in East African kala-azar., Proceedings of the 2nd Annual Medical Scientific Conference, KEMRI/KETRI, 1981, 54–81).

Blood biochemistry (Table 3) was not much altered at intake. With treatment, total blood bilirubin and BUN assays fell fradually, and serum albumin increased likewise.

Table 4 displays patient characteristics, drug effectiveness and drug safety data for the 3 treatment groups. The initial spleen aprasite grading averages 5+ in all three groups. At termination, all three groups yielded 100% clinical cures. Some partial cures occurred in patients treated with PM alone or SbV alone; even in those, however, spleen parasite gradings never exceeded 1+. All patients treated with PM+SbV made apparent cures.

The least incidence of relapses was seen in the PM treatment group, rising in the PM+SbV group and further in the SbV group; the difference between PM and SbV was highly significant (P<0.01).

The highest proportion of definite cures was seen in the PM+SbV treatment group, followed by the PM and SbV groups in that order. The cure rate at 6 months follow up examination was significantly higher in the PM and PM+SbV treatment groups than in the SbV group (

EXPERIMENTAL DISCUSSION

All three drug regimes resulted in the complete abatement of sings and symptoms (clinical cure) in all patients, with no detectable differences between treatment groups. Conversely, some important differences emerged in terms of parasitologic cures. Here the superiority of PM alone or combined with pentavalent antimonium is apparent. Treatment with SbV alone proved by far the least effective of all, with fully 45.5% failures. In the same experimental conditions PM alone or combined with SbV afforded the best results (Table 4). With the same treatment duration PM alone contributed the highest share of partial cures but also the smallest share of relapses, so that the total incidence of failures was only 21%. The combined PM+SbV regime resulted in materially earlier clearing of spleen parasites and produced the least failure rate (13% between partial cures and relapses). Thus the two drugs seem to act synergistically.

The optimal duration of SbV treatment is still the object of debate, apparently changing from one area to another and from one patient to another (WHO Expert Committee on Leishmaniasis, 1984 supra). In India, the duration of SbV treatment has been shown to correlate positively with the cure rate; in a comparative trial the best results (only 8% failures) were obtained with 20 mg SbV/kg daily administered for 40 days (Thakur et al, Rationalization of regimens of treatment of Kala-azar with sodium stibogluconate in India: a randomized study, British Medical Journal, 296, 1988, 1557–1559). Obviously a treatment period of that length would create compliance problems in the prevalent condition of tropical countries. In our own study the combined PM+SbV regime gave the best results (13% failure) when administered for an average 14 days. This, plus the low rate of relapses seen with PM administered alone for 19 days, suggests that the incidence of relapses with the PM+SbV regime might show further reduction by adding a few extra days of treatment.

The difference in terms of cure rates between SbV and PM alone or combined was highly significant (P<0.01). The choice between drug regimes may be based on cost and side effects consideration. PM is an inexpensive drug and caused no side effects in our study. SbV is expensive, more so for the PM+SbV combination where full dosage of both drugs are used. Furthermore, SbV produces distinctly more side effects. The synergism of action between PM and SbV makes it possible to obtain equally good therapeutic results with suitably reduced dosages, with obvious gains in terms of lower cost and fewer side effects. Additionally, the rate of definite cures might show further improvement with somewhat longer treatment periods, still materially shorter than those recommended for SbV therapy.

TABLE 2

| | Changes in the mean values of parametric indices during treatment and followup | | | | | | |
|---|---|---|---|---|---|---|---|
| | Eosinophil count/cu mm | Hemoglobin assay g/dl | Weight kg | Temp °C. | Heart rate/ minute | Spleen size (cm) | Parasite grading |
| Sbv | | | | | | | |
| Day 0 | 0 | 7.6 | 33.2 | 38.5 | 112 | 14.5 | 5 |
| Day 20 | 1 | 8.9 | 27.3 | 36.2 | 92 | 7 | 1 |

TABLE 2-continued

Changes in the mean values of parametric indices during treatment and followup

| | Eosinophil count/cu mm | Hemoglobin assay g/dl | Weight kg | Temp °C. | Heart rate/ minute | Spleen size (cm) | Parasite grading |
|---|---|---|---|---|---|---|---|
| Day 75 | 1 | 11.6 | 36.7 | 36.9 | 80 | 5 | 1 |
| PM | | | | | | | |
| Day 0 | 0 | 7.1 | 34.0 | 38.3 | 105 | 15.5 | 5 |
| Day 20 | 2 | 10.0 | 37.0 | 36.1 | 84 | 8.4 | 1 |
| Day 75 | 1 | 12.3 | 39.1 | 36.1 | 82 | 4.3 | 1 |
| PM + SbV | | | | | | | |
| Day 0 | 0 | 7.4 | 36.2 | 38.0 | 106 | 13.4 | 5 |
| Day 20 | 2 | 8.7 | 33.3 | 36.3 | 92 | 6.5 | 0 |
| Day 75 | 2 | 10.7 | 40.2 | 36.3 | 80 | 4.1 | 1 |

TABLE 3

Blood biochemistry data during the various treatments

| | ASAT I.U./l | ALAT I.U./l | ALP I.U./l | Bilirubin umol/l | BUN assay mmol/l | Creatinine umol/l | Albumin g/l |
|---|---|---|---|---|---|---|---|
| SbV | | | | | | | |
| Day 0 | 20.2 | 25.4 | 87.6 | 6.4 | 8.2 | 73.6 | 31.3 |
| Day 10 | 19.2 | 24.0 | 79.1 | 4.1 | 8.1 | 68.0 | 30.3 |
| Day 20 | 21.0 | 22.0 | 71.0 | 3.8 | 4.0 | 53.0 | 29.5 |
| Day 75 | 25.5 | 25.3 | 83.7 | 4.5 | 3.8 | 73.5 | 36.6 |
| Day 195 | 22.0 | 23.0 | 84.0 | 4.0 | 4.0 | 78.9 | 40.0 |
| PM | | | | | | | |
| Day 0 | 17.9 | 21.0 | 75.3 | 9.7 | 6.2 | 71.1 | 29.3 |
| Day 10 | 19.9 | 23.4 | 76.7 | 8.3 | 4.0 | 59.5 | 32.1 |
| Day 20 | 21.2 | 23.3 | 84.8 | 4.5 | 4.0 | 64.2 | 32.5 |
| Day 75 | 18.0 | 26.0 | 66.0 | 3.0 | 4.8 | 85.0 | 37.0 |
| Day 195 | 21.5 | 22.0 | 85.0 | 3.6 | 3.5 | 82.2 | 42.0 |
| PM + SbV | | | | | | | |
| Day 0 | 21.8 | 26.8 | 84.3 | 9.0 | 8.3 | 73.3 | 32.9 |
| Day 10 | 21.0 | 26.0 | 85.8 | 3.3 | 4.4 | 99.2 | 33.9 |
| Day 20 | 15.0 | 23.0 | 82.0 | 3.8 | 3.9 | 109.0 | 36.0 |
| Day 75 | 17.0 | 23.7 | 73.7 | 3.2 | 4.9 | 72.2 | 37.0 |
| Day 195 | 20.2 | 23.0 | 89.0 | 4.0 | 4.5 | 80.0 | 50.0 |

ASAT = Aspartate aminotransferase; ALAT = Alanine aminotransferase ALP = Alkaline phosphatase

TABLE 4

Patient characteristics, clinical results and parasitologic returns in the various treatment groups

| TREATMENT GROUPS | SbV | PM | PM + SbV |
|---|---|---|---|
| Mean age, years | 16.8 | 18.7 | 18.7 |
| (Range) | (4–48) | (5–49) | (3–63) |
| Male | 10 | 12 | 15 |
| Female | 1 | 7 | 8 |
| Totals | 11 | 19 | 23 |
| Mean treatment | | | |
| duration, days | 17 | 19 | 14 |
| Parasitic grading at intake | 5+ | 5+ | 5.+ |
| Clinical cures, No. (%) | 11 (100) | 19 (100) | 23 (100) |
| Partial cures, No. (%) | 1 (9.1) | 3 (15.8) | 0 (0) |
| Apparent cures, No. (%) | 10 (90.9) | 16 (84.2) | 23 (100) |
| Relapses, No. (%) | 4 (36.4) | 1 (5.2) | 3 (13) |
| Failures, No. (%) | 5 (45.5) | 4 (21) | 3 (13) |
| Definite cures, No. (%) | 6 (54.5) | 15 (79) | 20 (87) |
| Adverse effects, No. (%) | 3 (27) | 0 (0) | 5 (22) |

Apparent cure: negative spleen aspirate smears at termination of treatment;

Relapse: reappearance of leishmanial parasites after an apparent cure;

Definite cure: persisting clinical cure with negative spleen aspirates 6 months after termination of treatment;

Failures: partial cures and relapses.

Drug safety was assessed for each treatment regime in terms of incidence of drug-related signs and symptoms and of laboratory test results return abnormalities. The assembled data were processed statistically by the Fisher's exact test (chi-square) and Pearson's correlation coefficient.

Results

A total of 56 patients were entered. Of these, two died during the follow-up period, one from fulminating oral thrush and one from trauma, and one patient failed to report. This left 53 assessable patients, namely 37 males and 16 females, age range 3-36 years, mean age 18. Clinical manifestations at intake were fever, weakness, enlarged liver and spleen, pallor, and tachycardia in all patients; plus malnutrition in 95%, cough in 62%, jaundice in 25% and ankle oedema in 14%. Complicating factors present at intake or emerging in the course of treatment included epistaxis, pneumonia, uveltis throat infection, and chest pain, as reported in Chung et al., Complications of kala-azar and its treatment in Kenya, East African Medical Journal, 61, 1984, 120-127.

Fever was the first symptom to abate, usually after 24 to 60 hours of starting treatment; splenomegaly was the last. At 2 and 6 month follow-up examination, the spleen was still moderately enlarged respectively in 20 and 5% of treated patients. Body weight tended to drop in the first 10 days of treatment and pick up later, to return to normal by the first (2month) re-check (Table 4). Ankle oedema abated in the first 10 days of treatment.

The incidence of epistaxis was significantly reduced by treatment with vitamin K (10 mg daily for 5 days) in patients with low initial haemoglobin assays and prolonged prothrombin time readings. Uveitis with ocular pain and blurred vision was present at intake in 22,5% of the patients; it abated without specific treatment as visceral leishmaniasis was cured. Bouts of pneumonia developed in 9 cases (17%). Of these, 5 were on SbV alone and required antibiotic treatment; the remaining 4 were receiving PM and did not need additional antibiotic medication.

Initial hematologic disorders (Table 4) consisted for the most part of depressed hematopolesis (WHO Expert Committee on Leishmaniasis, Technical Report Series 70, 1984) and pancytopenia (Kasli, Haematological abnormalities in visceral leishmaniasis, East African Medical Journal, 57, 1980, 634-640; Wasunna et al., Haematological changes in patients with visceral leishmaniasis, Proceedings of the 12th International Congress of Tropical Medicine and Malaria, Abstract ThP 5-3, page 270); both features showed improvement as the underlying leishmaniasis was cured. All patients had zero eosinophil counts at intake; the reappearance of peripheral blood was taken to connote a good prognosis (Lyerly et al., Eosinophilis as prognostic indicator in East African kala-azar., Proceedings of the 2nd Annual Medical Scientific Conference, KEMRI/KETRI, 1981, 54-81).

Blood biochemistry (Table 5) was not much altered at intake. With treatment, total blood bilirubin and BUN assays fell gradually, and serum albumin increased likewise.

Table 6 displays patient characteristics, drug effectiveness and drug safety data for the 3 treatment groups. The initial spleen parasite grading averaged 5+ in all three groups. At termination, all three groups yielded 100% clinical cures. Some partial cures occurred in patients treated with PM alone or SbV alone; even in those, however, spleen parasite gradings never exceeded 1+. All patients treated with PM+SbV made apparent cures.

The least incidence of relapses was seen in the PM treatment group, rising in the PM+SbV group and further in the SbV group; the difference between PM and SbV was highly significant (P<0.01).

The highest proportion of definite cures was seen in the PM+SbV treatment group followed by the PM and SbV groups in that order. The cure rate at 6 months follow up examination was significantly higher in the PM and PM+SbV treatment groups than in the SbV group (P<0.01 for both differences).

EXPERIMENTAL DISCUSSION

All three drug regimes resulted in the complete abatement of signs and symptoms (clinical cure) in all patients, with no detectable differences between treatment groups. Conversely, some important differences emerged in terms of parasitologic cures. Here the superiority of PM alone or combined with pentavalent antimonium is apparent. Treatment with SbV alone proved by far the least effective of all, with fully 45.% failures. In the same experimental conditions PM alone or combined with SbV afforded the best results (Table 6). With the same treatment duration PM alone contributed the highest share of partial cures but also the smallest share of relapses, so that the total incidence of failures was only 21%. The combined PM+SbV regime resulted in materially earlier clearing of spleen parasites and produced the least failure rate (13% between partial cures and relapses). Thus the two drugs seem to act synergistically.

The optimal duration of SbV treatment is still the object of debate, apparently changing from one area to another and from one patient to another (WHO Expert Committee on Leishmaniasis, 1984 supra). In India, the duration of SbV treatment has been shown to correlate positively with the cure rate; in a comparative trial the best results (only 8% failures) were obtained with 20 mg SbV/kg daily administered for 40 days (Thakur et al, Rationalization of regimens of treatment of Kala-azar with sodium stibogluconate in India: a randomized study, British Medical Journal, 296, 1988, 1557-1559). Obviously a treatment period of that length would create compliance problems in the prevalent condition of tropical countries. In our own study the combined PM+SbV regime gave the best results (13% failure) when administered for an average 14 days. This, plus the low rate of relapses seen with PM administered alone for 19 days, suggests that the incidence of relapses with the PM+SbV regime might show further reduction by adding a few extra days of treatment.

The difference in terms of cure rates between SbV and PM alone or combined was highly significant (P<0.01). The choice between drug regimes may be based on cost and side effects considerations. PM is an inexpensive drug and caused no side effects in our study. SbV is expensive, more so for the PM+SbV combination where full dosage of both drugs are used. Furthermore, SbV produces distinctly more side effects. The synergism of action between PM and SbV makes it possible to obtain equally good therapeutic results with suitably reduced dosages, with obvious gains in terms of lower cost and fewer side effects. Additionally, the rate of definite cures might show further improvement with somewhat longer treatment periods, still materially shorter than those recommended for SbV therapy.

TABLE 4

Changes in the mean values of parametric indices during treatment and followup

| | Eosinophil count/cu mm | Hemoglobin assay g/dl | Weight kg | Temp °C. | Heart rate/ minute | Spleen size (cm) | Parasite grading |
|---|---|---|---|---|---|---|---|
| Sbv | | | | | | | |
| Day 0 | 0 | 7.6 | 33.2 | 38.5 | 112 | 14.5 | 5 |
| Day 20 | 1 | 8.9 | 27.3 | 36.2 | 92 | 7 | 1 |
| Day 75 | 1 | 11.6 | 36.7 | 36.9 | 80 | 5 | 1 |
| PM | | | | | | | |
| Day 0 | 0 | 7.1 | 34.0 | 38.3 | 105 | 15.5 | 5 |
| Day 20 | 2 | 10.0 | 37.0 | 36.1 | 84 | 8.4 | 1 |
| Day 75 | 1 | 12.3 | 39.1 | 36.1 | 82 | 4.3 | 1 |
| PM + SbV | | | | | | | |
| Day 0 | 0 | 7.4 | 36.2 | 38.0 | 106 | 13.4 | 5 |
| Day 20 | 2 | 8.7 | 33.3 | 36.3 | 92 | 6.5 | 0 |
| Day 75 | 2 | 10.7 | 40.2 | 36.3 | 80 | 4.1 | 1 |

TABLE 5

Blood biochemistry data during the various treatments

| | ASAT I.U./l | ALAT I.U./l | ALP I.U./l | Bilirubin umol/l | BUN assay mmol/l | Creatinine umol/l | Albumin g/l |
|---|---|---|---|---|---|---|---|
| SbV | | | | | | | |
| Day 0 | 20.2 | 25.4 | 87.6 | 6.4 | 8.2 | 73.6 | 31.3 |
| Day 10 | 19.2 | 24.0 | 79.1 | 4.1 | 8.1 | 68.0 | 30.3 |
| Day 20 | 21.0 | 22.0 | 71.0 | 3.8 | 4.0 | 53.0 | 29.5 |
| Day 75 | 25.5 | 25.3 | 83.7 | 4.5 | 3.8 | 73.5 | 36.6 |
| Day 195 | 22.0 | 23.0 | 84.0 | 4.0 | 4.0 | 78.9 | 40.0 |
| PM | | | | | | | |
| Day 0 | 17.8 | 21.0 | 75.3 | 9.7 | 6.2 | 71.1 | 29.3 |
| Day 10 | 19.9 | 23.4 | 76.7 | 8.3 | 4.0 | 59.5 | 32.1 |
| Day 20 | 21.2 | 23.3 | 84.8 | 4.5 | 4.0 | 64.2 | 32.5 |
| Day 75 | 18.0 | 26.0 | 66.0 | 3.0 | 4.8 | 85.0 | 37.0 |
| Day 195 | 21.5 | 22.0 | 85.0 | 3.6 | 3.5 | 82.2 | 42.0 |
| PM + SbV | | | | | | | |
| Day 0 | 21.8 | 26.8 | 84.3 | 9.0 | 8.3 | 73.3 | 32.9 |
| Day 10 | 21.0 | 26.0 | 85.8 | 3.3 | 4.4 | 99.2 | 33.9 |
| Day 20 | 15.0 | 23.0 | 82.0 | 3.8 | 3.9 | 109.0 | 36.0 |
| Day 75 | 17.0 | 23.7 | 73.7 | 3.2 | 4.9 | 72.2 | 37.0 |
| Day 195 | 20.2 | 23.0 | 89.0 | 4.0 | 4.5 | 80.0 | 50.0 |

ASAT = Aspartate aminotransferase; ALAT = Alanine aminotransferase ALP = Alkaline phosphatase

TABLE 6

Patient characteristics, clinical results and parasitologic returns in the various treatment groups

| TREATMENT GROUPS | SbV | PM | PM + SbV |
|---|---|---|---|
| Mean age, years | 16.8 | 18.7 | 18.7 |
| (Range) | (4–48) | (5–49) | (3–63) |
| Male | 10 | 12 | 15 |
| Female | 1 | 7 | 8 |
| Totals | 11 | 19 | 23 |
| Mean treatment duration, days | 17 | 19 | 14 |
| Parasitic grading at intake | 5+ | 5+ | 5+ |
| Clinical cures, No. (%) | 11 (100) | 19 (100) | 23 (100) |
| Partial cures, No. (%) | 1 (9.1) | 3 (15.8) | 0 (0) |
| Apparent cures, No. (%) | 10 (90.9) | 16 (84.2) | 23 (100) |
| Relapses, No. (%) | 4 (36.4) | 1 (5.2) | 3 (13) |
| Failures, No. (%) | 5 (45.5) | 4 (21) | 3 (13) |
| Definite cures, No. (%) | 6 (54.5) | 15 (79) | 20 (87) |
| Adverse effects, No. (%) | 3 (27) | 0 (0) | 5 (2) |

We claim:

1. A method of treatment of visceral leishmaniasis which comprises administering parenterally to a subject suffering therefrom, paromomycin or a non-toxic acid addition salt thereof, and sodium stibogluconate, in a weight ratio of from 1:9 to 9:1.

2. A method according to claim 1, wherein the acid addition salt is the sulphate.

3. A method according to claim 1, wherein the weight ratio is from 4:6 to 6:4.

4. A method according to claim 3, wherein the weight ratio is about 4:5 and wherein the paromomycin or salt thereof is administered to the subject in an amount of about 16 mg/kg body weight/day and the sodium stibogluconate is administered to the subject in an amount of about 20 mg/kg body weight/day.

5. A composition suitable for parenteral administration for the treatment of visceral leishmaniasis, which composition comprises paromomycin or a non-toxic acid addition salt thereof, sodium stibogluconate and a pharmaceutically acceptable diluent, the weight ratio of the paromomycin or salt thereof to the sodium stibogluconate being from 1:9 to 9:1.

6. A composition according to claim 5, wherein the weight ratio is from 4:6 to 6:4.

* * * * *

UNITED STATES PATENT AND TRADEMARK OFFICE
CERTIFICATE OF CORRECTION

PATENT NO. : 5,470,836
DATED : November 28, 1995
INVENTOR(S) : Luigi DONNO, et al.

It is certified that error appears in the above-indentified patent and that said Letters Patent is hereby corrected as shown below:

On the title page, Item [54], the title should read:

--PAROMOMYCIN OR ITS DERIVATIVES OR SALTS THEREOF IN COMBINATION WITH SODIUM STIBOGLUCONATE FOR PARENTERAL TREATMENT OF HUMAN PARASITIC DISEASES-- and Item [63], the Related U.S. Application Data should read:

--Continuation of Ser. No. 86,565, Jul. 6, 1993, abandoned, which is a continuation of Ser. No. 943,139, Sep. 10, 1992, abandoned, which is a continuation of Ser. No. 598,611, Oct. 25, 1990, abandoned.--

Signed and Sealed this

Fourth Day of June, 1996

*Attest:*

BRUCE LEHMAN

*Attesting Officer*     *Commissioner of Patents and Trademarks*